United States Patent
Shinabe et al.

(12)
(10) Patent No.: US 6,456,055 B2
(45) Date of Patent: Sep. 24, 2002

(54) PARTICLE MEASUREMENT APPARATUS AND METHOD

(75) Inventors: Seiya Shinabe, Kobe; Kunio Ueno, Kakogawa, both of (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/805,208

(22) Filed: Mar. 14, 2001

(30) Foreign Application Priority Data

Mar. 14, 2000 (JP) ........................................ 2000-070479

(51) Int. Cl.$^7$ .............................................. G01N 27/00
(52) U.S. Cl. ........................................ 324/71.4; 73/1.02
(58) Field of Search ................................ 356/335, 336; 73/1.02; 324/71.4, 615, 76.51

(56) References Cited

U.S. PATENT DOCUMENTS

| | | | | |
|---|---|---|---|---|
| 3,806,809 A | * | 4/1974 | Firman | 324/76.51 |
| 5,327,129 A | * | 7/1994 | Soenen | 324/615 |
| 5,506,673 A | * | 4/1996 | Kosaka | 356/336 |

FOREIGN PATENT DOCUMENTS

| | | |
|---|---|---|
| JP | A2206905 | 8/1990 |
| JP | A7147518 | 6/1995 |

* cited by examiner

*Primary Examiner*—Christine Oda
(74) *Attorney, Agent, or Firm*—Birch, Stewart, Kolasch & Birch, LLP

(57) ABSTRACT

A particle measurement apparatus includes: a particle signal detector for detecting a particle signal; a false signal generator for generating a false signal corresponding to the particle signal; a selector for selecting the particle signal or the false signal, a non-linear amplifier; a first calculator for receiving the signal selected by the selector through the non-linear amplifier to calculate a characteristic parameter; a second calculator for receiving the signal selected by the selector not through the non-linear amplifier to calculate the characteristic parameter; a comparator for including the characteristic parameters calculated by the first and second calculators respectively when the selector selects the false signal; a memory for storing a comparison result of the comparator; and a compensator for compensating the characteristic parameter calculated by the first calculator on the basis of the comparison result when the selector selects the particle signal.

13 Claims, 2 Drawing Sheets

PARTICLE MEASUREMENT APPARATUS AND METHOD

CROSS-REFERENCE TO RELATED APPLICATION

This application is related to Japanese Patent Application No. 2000-70479 filed on Mar. 14, 2000, whose priority is claimed under 35 USC §119, the disclosure of which is incorporated by reference in its entirety.

BACKGROUND OF THE INVENTION

1. Field of the Invention

The present invention relates to a particle measurement apparatus and method and more particularly to an apparatus and method for calculating a characteristic parameter by processing a signal representative of particle characteristics through a nonlinear amplifier.

2. Description of the Related Art

Particle measurement apparatuses usually employ a linear amplifier for amplifying an electrical signal obtained from particles, i.e., a particle signal to be measured.

The linear amplifier used in such apparatuses is required to maintain the precision of linearity for accurate measurements. Therefore some techniques to compensate or correct the amplification characteristics of the linear amplifier are conventionally proposed (see, Japanese unexamined patent publication Nos. Hei 7(1995)-147518 and Hei 2(1990)-206905). a non-linear amplifier, e.g., a logarithmic amplifier rather than the linear amplifier. It is because the industrial particles have a wide range of diameter from submicrons to hundreds of microns and the non-liner amplifier can conveniently cover the wide range.

However, few techniques for compensating the amplification characteristics of the non-linear amplifier have been known.

SUMMARY OF THE INVENTION

In view of such circumstances, it is an object of the present invention to provide a particle measurement apparatus and method in which the characteristics of the non-linear amplifier used for processing the particle signal are compensated so as to permit a wide range particle measurement with high precision.

The object of the present invention is attained by providing a particle measurement apparatus comprising: a particle signal detecting section for detecting a particle signal with respect to a plurality of particles, the particle signal representing characteristics of each particle; a false signal generating section for generating a false signal corresponding to the particle signal; a selecting section for selecting the particle signal or the false signal, a non-linear amplifier; a first calculating section for receiving the signal selected by the selecting section through the non-linear amplifier to calculate a characteristic parameter; a second calculating section for receiving the signal selected by the selection section not through the non-linear amplifier to calculate the characteristic parameter; a comparison section for comparing the characteristic parameters calculated by the first and second calculating sections respectively when the selecting section selects the false signal; a storage section for storing a comparison result of the comparison section; and a compensating section for compensating the characteristic parameter calculated by the first calculating section on the basis of the comparison result when the selection section selects the particle signal.

In other words, the apparatus of the present invention is so constituted as to check an input-output characteristics of the non-linear amplifier using a false signal beforehand so that when a real particle signal is amplified by the non-linear amplifier to calculate the characteristic parameter of the particle, a result of the calculation may be compensated using the aforesaid input-output characteristics.

BRIEF DESCRIPTION OF THE DRAWINGS

A preferred embodiment of the present invention will be illustrated, and not by way of limitation, in conjunction with the accompanying drawings, in which.

DESCRIPTION OF THE PREFERRED EMBODIMENTS

Figure 1:
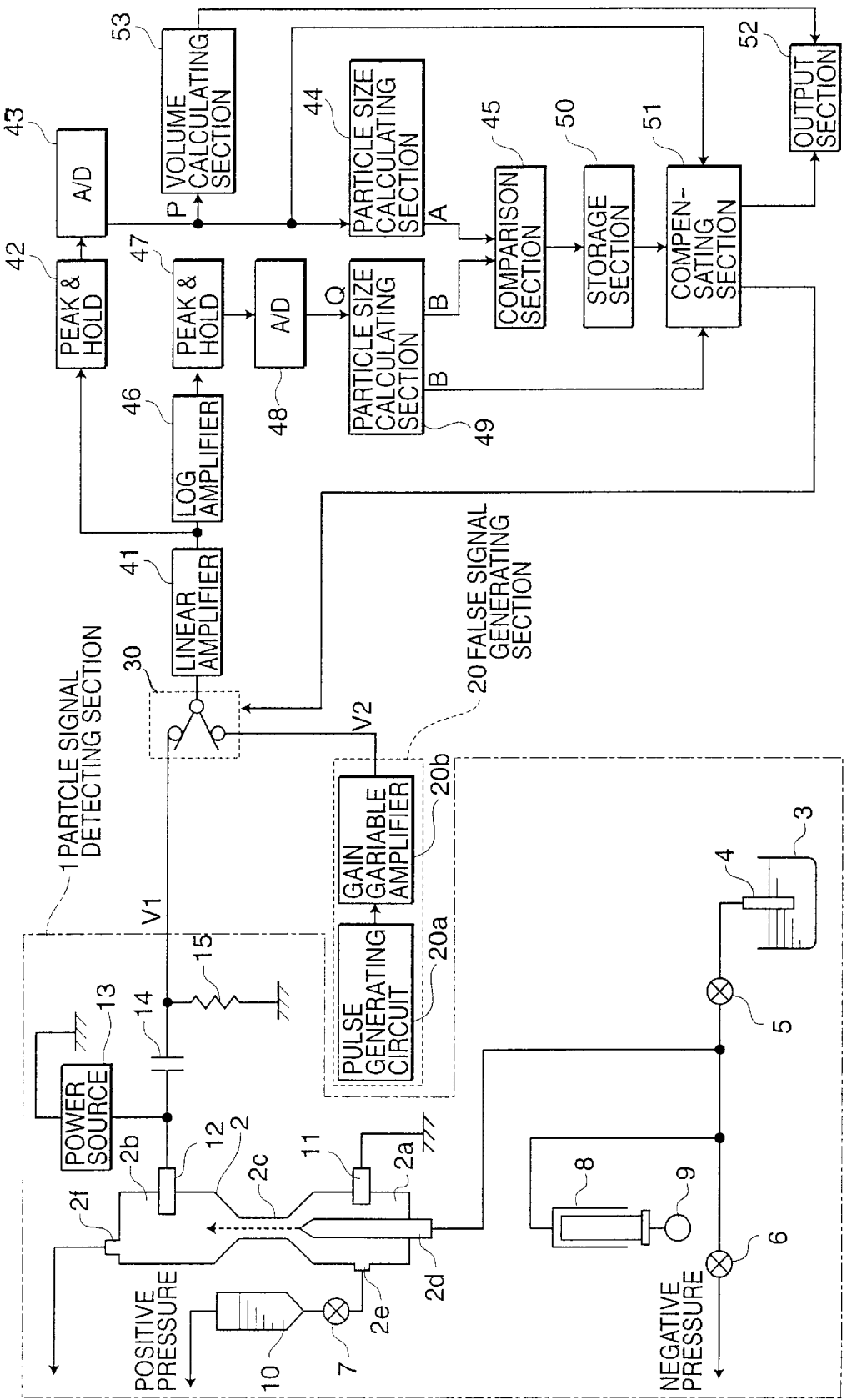
FIG. 1 is a block diagram of a particle measurement apparatus embodying the present invention.

The object particles to be measured in the present invention include a toner, graphite, silica, abrasive material, ceramic powder, pigment, powder paint, cultured cell, blood cell, yeast, plankton and magnetic powder. The particle size in diameter ranges from submicrons to hundreds of microns.

In the present invention, the particle signal detecting section which individually detects the characteristics of a plurality of particles and convert them into a particle signal may be an optical flow cytometer-type detector in which a solution containing particles is flowed into a sheath flow cell to detect optical information from the particles or an electric measurement-type detector wherein a solution containing particles is flowed through an orifice (microscopic hole) to detect a change in electrical impedance of the particle-contained solution, for example.

The detecting section detects and converts the characteristics of particles into a particle signal. This particle signal is an analog pulse signal, for example. In case the optical flow cytometer-type detector is used as the detecting section, the signal shows a change in time of the intensity of such light rays as forward scattered, side scattered and fluorescent lights from the particles. In case the electric measurement-type detector is used as the detecting section, its signal shows a change in time of the electric impedance.

In the false signal generating section for generating false signals, a signal generator may be used that generates an analogue signal, for example, a pulse-formed signal corresponding to a plurality of particles different in size and kind to be detected by the particle signal detecting section.

The selecting section is provided with a switching function, for which an analog switch, for example, may be used. As non-linear amplifier may be used a logarithmic amplifier TL441 (Texas Instruments), for example. Some of the same type amplifiers may be combined (for example, by cascade connection) to expand its input-output range.

The first calculating section receives a signal (particle signal or false signal) selected by the selecting section through the non-linear amplifier and calculates the characteristic parameters. The second calculating section receives a signal selected by the selecting section not through the non-linear amplifier and calculates the characteristic parameters. The calculated parameters may include sampling values such as, for example, a signal peak value (pulse height) and pulse width, or a particle volume and particle diameter calculated on the basis thereof.

Since the first calculating section calculates the characteristic parameters on the basis of the particle signal or false signal through the non-linear amplifier, the calculated parameters will be values that require to be corrected depending on the input-output characteristics of the non-linear amplifier. On the other hand, the second calculating section calculates the characteristic parameters from a false signal not through the non-linear amplifier, and therefore, the calculated parameters will be highly accurate values. But the calculation has to be performed using a mathematical non-linear function instead of the non-linear amplifier. Thus, the calculation process is complicated and takes longer than the process of the first calculating section.

The comparison section compares two kinds of characteristic parameters calculated by the first and second calculating sections respectively when the selecting section selects the false signal. In that case, the two kinds of characteristic parameters may be compared by converting them into a correction curve on a rectangular coordinates. Also, a correction table or the like may be prepared to calculate a difference between the two kinds of parameters for comparison.

The storage section preferably comprises rewritable memory such a RAM, since the storage section stores renewably the aforesaid correction curve or correction table.

It is noted that the first and second calculating sections, comparison section, storage section, compensating section may be integrally formed using a personal computer or microcomputer.

In another aspect, the present invention provides a method of measuring particles, comprising the steps of: making a preparation for measurement by sucking a sample liquid containing particles to introduce the same into a particle signal detector; generating a false signal corresponding to a particle signal which really represents characteristics of a plurality of particle; calculating a first characteristic parameter by receiving the false signal through a non-linear amplifier; calculating a second characteristic parameter by receiving the false signal not through the non-linear amplifier; comparing the first characteristic parameter with the second characteristic parameter; storing a comparison result; detecting a particle signal by the particle detector; calculating a third characteristic parameter by receiving the detected particle signal through the non-linear amplifier; and correcting the third characteristic parameter on the basis of the comparison result.

The step of making the measurement preparation may include sampling, that is, sucking a sample liquid to introducing it into the particle detector, and processing the sample liquid, for example, diluting or reacting it with a reagent. If the step of storing the comparison results is completed during the step of making the measurement preparation, the step of correcting the parameter can be carried out conveniently and efficiently. The effect of the ambient temperature on the non-linear amplifier can be properly corrected.

Configuration and Operation of Particle Signal Detecting Section

In the present embodiment, an electric measurement (electrical sensing zone method) is used for a particle signal detecting section 1. The particle signal detecting section 1 is composed of a flow cell 2, a container 3 for storing a sample liquid containing particles to be tested, a suction nozzle 4 for sucking the sample liquid, valves 5, 6, 7, a syringe 8 actuated by a motor 9 and a sheath liquid container 10. The flow cell 2 is formed of a first cell 2a, a second cell 2b, an orifice section 2c having a micro through hole (orifice) through which the first cell 2a communicates with the second cell 2b and a sample nozzle 2d for jetting the sample liquid into the orifice section 2c. Furthermore, the first cell 2a is provided with a inlet port 2e which accepts a sheath liquid from the sheath liquid container 10 through the valve 7. And the second cell 2b is provided with a outlet port 2f which discharges the sheath liquid together with the sample liquid.

Furthermore, the first cell 2a and the second cell 2b are provided with electrodes 11, 12 respectively. A power source 13 is provided for supplying a constant d.c. current to the liquid between the electrodes 11 and 12. When a voltage is generated between the electrode 12 and the electrode 11, a d.c. component of the voltage is cut out by a capacitor 14 and a resistor 15, and an a.c. component (fluctuating component) alone is outputted as a particle signal V1.

In the particle signal detecting section 1, if the valves 5, 6 are first opened for a predetermined period of time, the sample liquid is sucked through the suction nozzle 4 under a negative pressure until a flow path between the valves 5, 6 is filled with the sample liquid. Then, the sample liquid is discharged into the first cell 2a through the sample nozzle 2d when the syringe 8 presses out the sample liquid between the valves 5, 6 to the sample nozzle 2d at a constant rate.

If the valve 7 is opened at the same time, the sheath liquid is supplied to the first cell 2a. Thus, the sample liquid is sheathed with the sheath liquid, and further squeezed by the orifice section 2c to form a sheath flow.

The formed sheath flow allows the particles contained in the sample liquid to be aligned and flowed in a line through the orifice section 2c. The sample liquid and the sheath liquid that have passed through the orifice section 2c are discharged through the outlet port 2f of the second cell 2b.

The electric impedance of the liquid between the electrodes 11 and 12 is determined by an electrical conductivity of the sheath liquid , a size (sectional area) of the orifice in the orifice section 2c, an electrical conductivity of the sample liquid and a diameter of the flow of the sample liquid.

As mentioned above, the d.c. current is supplied to the liquid between the electrode 12 and the electrode 11 from the power source 13, a d.c. voltage is generated that is determined by an electrical resistance and electric current value between the electrode 12 and the electrode 11. Furthermore, if the particles pass through the orifice section 2c, an electric resistance at both ends of the orifice section 2c changes. Therefore, the voltage generated between the electrode 12 and the electrode 11 changes in the form of pulse every time a particle passes. The maximum value of change (peak value of the pulse) is proportional with a size of the particle passing through the orifice section 2c. Thus, the particle signal V1 represents such pulses.

Configuration and Operation of False Signal Generating Section

Meanwhile, a false signal generating section 20 is provided with a pulse generating circuit 20a and a gain variable amplifier 20b. The amplifier 20 changes pulse waveforms outputted from the pulse generating circuit 20a and generates a false signal V2 including a plurality of serial pulse waveforms corresponding to the particle signal V1.

The particle signal V1 and false signal V2 are selected by a selecting section 30 and processed in the following way.

Step of Measuring False Signal

In the particle measurement apparatus of the present embodiment, the selecting section 30 first selects the false signal V2, and the step of measuring the false signal V2 is carried out. The false signal V2 can be corresponds to a particle signal representative of a plurality of particles of all sizes from the largest to the smallest to be detected in the step of measuring the particle signal, which will be described later. That is, the false signal V2 corresponds to a plurality of saw-tooth pulses with different peak values which will be obtained from particles within a volume range of 10 to $10^5$ fl.

Then, the false signal V2 selected by the selecting section 30 is amplified by a linear amplifier 41 and its peak value is sampled and hold by a peak hold circuit 42 and converted into a digital value P by an A/D converter 43, then inputted into a particle size calculating section 44.

Meanwhile, if the particle is spherical, then the relation between a volume V and a particle diameter D is given by the following equation:

$$V = (\pi/6) \cdot D^3 \qquad (1)$$

Since the peak value P corresponds to the particle volume, $$V = k_1 \cdot P \qquad (2)$$

From (1) and (2), $$D = k_2 \cdot P^{1/3} \qquad (3)$$

(3) is transformed as follows.

$$D = k_3 \cdot \mathrm{LOG} P + k_4 \qquad (4)$$

($k_1$, $k_2$, $k_3$, $k_4$: constants)

Therefore, the particle size calculation section 44 receives the output P from the A/D converter 43, calculates the particle diameter D using equation (4) and outputs a result A to a comparison section 45.

Also, the false signal amplified by the linear amplifier 41 is logarithmically converted by an LOG amplifier (logarithmic amplifier) 46, and peak values are sampled and held by the peak hold circuit 47, converted into a digital value Q by the A/D converter 43 and inputted into a particle size calculating section 49.

The particle size calculating section 49 calculates a particle diameter D by equation (4). In this case, the LOG amplifier 46 allows an output Q of the A/D converter 48 to be given as follows:

$$Q = \mathrm{LOG} P \qquad (5)$$

Therefore, from equations (4), (5), $$D = k_3 \cdot Q + k_4 \qquad (6)$$

Then, the particle size calculating section 49 calculates the particle diameter D using equation (6) and outputs a result value B to a comparison section 45.

Figure 2:
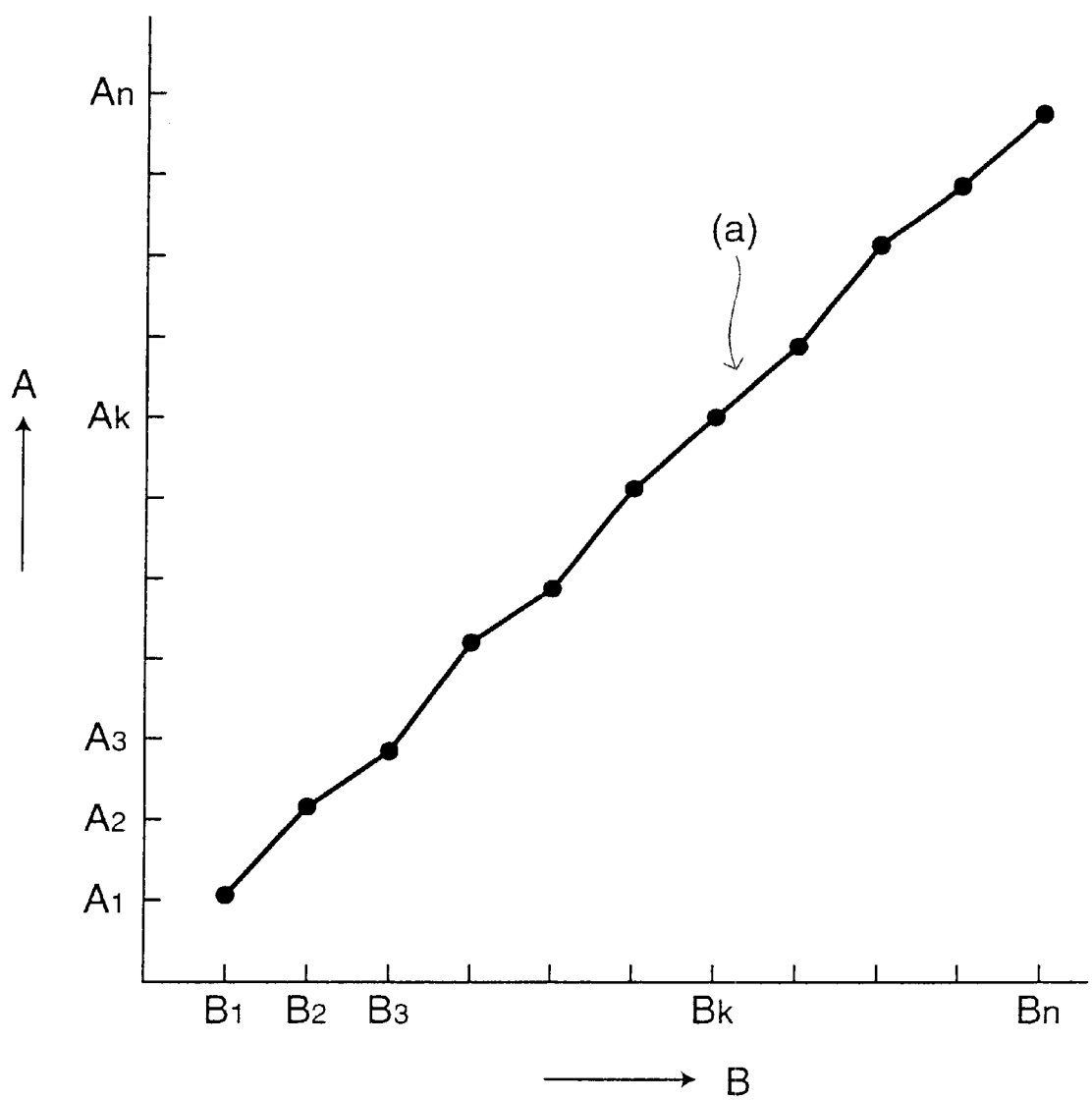
FIG. 2 is a correction curve in the embodiment.

With regard to n pieces of false pulses outputted from the false signal generating section 20, as shown in FIG. 2, the comparison section 45 plots on A–B two-dimensional coordinates n points representative of particle diameter $A_1$, $A_2$, ... $A_n$, and $B_1$, $B_2$, ... $B_n$ obtained from the particle size calculating sections 44 and 49, respectively and prepares a correction curve (a) by linear interpolation between the plotted points and stores it in a storage section 50.

Step of Measuring Particle Signal

In this step, the sample liquid is flowed into the flow cell 2 while the selecting section 30 selects the particle signal V1. Thus, the measurement of the particle signal is carried out. The particle signal V1 is amplified by the linear amplifier 41 and logarithmically converted by the LOG amplifier 46. The peak values is sampled and hold by the peak hold circuit 47, converted into a digital value Q by the A/D converter 43 and inputted into the particle size calculating section 49.

The particle size calculating section 49 calculates the particle diameter D using the equation (6) and outputs its value as B into the compensating section 51. The compensating section 51 corrects m pieces of particle diameters B obtained from the particle size calculating section 49, that is, particle diameters B are converted into particle diameters A respectively using the correction curve in FIG. 2. An output section 52 prepares a particle size distribution on the basis of m pieces of the corrected particle diameters and displays it.

Also, the particle signal V1 is amplified by the linear amplifier 41, its peak values are sampled and hold by the peak hold circuit 42 and is converted into digital values P by the A/D converter 43 to be inputted into a volume calculating section 53. The volume calculating section 53 converts m pieces of peak values P into respective volumes V using the equation (2). The output section 52 prepares a particle volume distribution on the basis of m pieces of particle volumes and displays it.

As set forth above, the particle diameters D can be calculated by the simple linear equation (6) at a high speed, and the calculated values are speedily corrected by the correction curve in FIG. 2. That is, the input-output characteristics of the LOG amplifier 46 can be easily and precisely compensated. Therefore, a wide range of particle sizes can be calculated with high precision and at a high speed.

The input-output characteristics of the logarithmic amplifier tend to be affected by the ambient temperature, and therefore it is desirable to renew the correction curve in FIG. 2 beforehand by carrying out the false signal detecting step before the particle signal detecting step.

It is noted that the present embodiment uses two peak hold circuits and two A/D converters. But if it is so arranged that a signal to be inputted into the peak hold circuits 42, 47 is selected by a switch, one peak hold circuit and one A/D converter can be omitted.

The gain variable amplifier 20b may be provided within linear amplifier 41. In that case, the gain variable amplifier 20b can have two functions, one being for changing the peak values of the false signal and the other being for varing the gain in measuring the particle signal.

According to the present invention, even if the particle signal is amplified through the non-linear amplifier, the input-output characteristics of the non-linear amplifier are compensated sufficiently, permitting measurement of particles over a wide size range with high accuracy.

What is claimed is:

1. A particle measurement apparatus comprising:
    a particle signal detecting section for detecting a particle signal with respect to a plurality of particles, the particle signal representing characteristics of each particle;
    a false signal generating section for generating a false signal corresponding to the particle signal;
    a selecting section for selecting the particle signal or the false signal,
    a non-linear amplifier;
    a first calculating section for receiving the signal selected by the selecting section through the non-linear amplifier to calculate a characteristic parameter;
    a second calculating section for receiving the signal selected by the selection section not through the non-linear amplifier to calculate the characteristic parameter;
    a comparison section for comparing the characteristic parameters calculated by the first and second calculating sections respectively when the selecting section selects the false signal;

a storage section for storing a comparison result of the comparison section; and a compensating section for compensating the characteristic parameter calculated by the first calculating section on the basis of the comparison result when the selection section selects the particle signal.

2. The particle measurement apparatus of claim 1, wherein the particle signal detecting section comprises an electric measurement particle detector.

3. The particle measurement apparatus of claim 1, wherein the non-linear amplifier comprises a logarithmic amplifier.

4. The particle measurement apparatus of claim 1, wherein the false signal generating section comprises a pulse generating circuit and a gain variable amplifier.

5. The particle measurement apparatus of claim 1, wherein the selecting section comprises an analog switch.

6. The particle measurement apparatus of claim 1, wherein the second calculating section calculates the characteristic parameter using a mathematical non-linear function.

7. The particle measurement apparatus of claim 1, wherein the characteristics parameter comprises a pulse height and pulse width or a particle volume and particle diameter calculated on the basis thereof.

8. The particle measurement apparatus of claim 1, wherein the storage section comprises a ROM.

9. The particle measurement apparatus of claim 1, wherein the comparison result is stored as a correction curve on rectangular coordinates.

10. The particle measurement apparatus of claim 1, further comprising a first A/D converter for beforehand converting the signal input to the first calculating section into a digital signal and a second A/D converter for beforehand converting the signal input to the second calculating section into a digital signal.

11. A method of measuring particles, comprising the steps of:

making a preparation for measurement by sucking a sample liquid containing particles to introduce the same into a particle signal detector;

generating a false signal corresponding to a particle signal which really represents characteristics of a plurality of particles;

calculating a first characteristic parameter by receiving the false signal through a non-linear amplifier;

calculating a second characteristic parameter by receiving the false signal not through the non-linear amplifier;

comparing the first characteristic parameter with the second characteristic parameter;

storing a comparison result;

detecting a particle signal by the particle detector;

calculating a third characteristic parameter by receiving the detected particle signal through the non-linear amplifier; and correcting the third characteristic parameter on the basis of the comparison result.

12. The method of claim 11, wherein the steps from the false signal generating step to the storing step are carried out along with the measurement preparations step.

13. The method of claim 11 which is carried out by the apparatus of claim 1.

* * * * *